USO10130698B2

(12) United States Patent
Fachinger et al.

(10) Patent No.: US 10,130,698 B2
(45) Date of Patent: *Nov. 20, 2018

(54) VACCINE AGAINST PORCINE CIRCO VIRUS TYPE 2

(71) Applicant: Intervet Inc., Madison, NJ (US)

(72) Inventors: Vicky Fachinger, Bad Soden (DE); Melanie Sno, Venlo (NL); Maarten Hendrik Witvliet, Oostrum (NL)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/038,765

(22) PCT Filed: Dec. 2, 2014

(86) PCT No.: PCT/EP2014/076224
§ 371 (c)(1),
(2) Date: May 24, 2016

(87) PCT Pub. No.: WO2015/082458
PCT Pub. Date: Jun. 11, 2015

(65) Prior Publication Data
US 2017/0157236 A1    Jun. 8, 2017

(30) Foreign Application Priority Data

Dec. 3, 2013    (EP) ..................... 13195515

(51) Int. Cl.
| | | |
|---|---|---|
| *A61K 39/12* | (2006.01) | |
| *A61K 39/02* | (2006.01) | |
| *C12N 7/00* | (2006.01) | |
| *A61K 39/00* | (2006.01) | |

(52) U.S. Cl.
CPC .......... *A61K 39/12* (2013.01); *A61K 39/0241* (2013.01); *A61K 39/105* (2013.01); *C12N 7/00* (2013.01); *A61K 2039/54* (2013.01); *A61K 2039/552* (2013.01); *A61K 2039/55566* (2013.01); *A61K 2039/70* (2013.01); *C12N 2750/10034* (2013.01)

(58) Field of Classification Search
None
See application file for complete search history.

(56) References Cited

U.S. PATENT DOCUMENTS

2006/0233831 A1 * 10/2006 Parisot .................. A61K 39/39
424/204.1
2013/0266603 A1   10/2013 Nitzel

FOREIGN PATENT DOCUMENTS

| EP | 1958644 A1 | 8/2008 |
|---|---|---|
| WO | WO0001409 A2 | 1/2000 |
| WO | WO2005009462 A2 | 2/2005 |
| WO | WO2007028823 A1 | 3/2007 |
| WO | WO2007094893 A2 | 8/2007 |
| WO | WO2008076915 A2 | 6/2008 |
| WO | WO2009126356 A2 | 10/2009 |
| WO | WO2009127684 A1 | 10/2009 |
| WO | WO2013152083 A2 | 10/2013 |

OTHER PUBLICATIONS

APVS Vietnam, Sep. 23-25, 2013, Tacker, B et al, Diagnostic laboratory survey of porcine circovirus type 2 and mycoplasma hyopneumoniae maternally derived antibodies.
Gamage, L et al, Immonugenicity of Bacteriophage Lambda Particles Displaying Porcine Circovirus 2 (PCV2) Capsid Protein Apitopes, Vaccine, Nov. 5, 2009, p. 6595-6604, vol. 27, No. 47, Elsevier.
International Search report for PCTEP 2014 076244 dated Feb. 6, 2015, 5 pages.
T Opriessnig et al, Effect of porcine circovirus type 2 (PCV2) vaccination on porcine reproductive and reproductive and respiratory yndrome virus (PRRSV) and PCV2 coinfection, Veterinary Microbiology, 2008, pp. 103-114, vol. 131, Elsevier.
Eble, et al, Intradermal Vaccination of Pigs Against FMD With 1/10 Dose Results in Comparable Vaccine Efficacy As Intramuscular Vaccination With a Full Dose, Vaccine, 2009, pp. 1272-1278, vol. 27, Elsevier, JP.

* cited by examiner

*Primary Examiner* — Brian Gangle (57) ABSTRACT

The present invention pertains to a vaccine comprising a non-replicating immunogen of porcine circo virus type 2 for use in prophylactically treating an animal that has circulating antibodies directed against porcine circo virus type 2, against an infection with pathogenic porcine circo virus type 2 by a single dose administration of the vaccine into the dermis of the animal.

6 Claims, 5 Drawing Sheets

VACCINE AGAINST PORCINE CIRCO VIRUS TYPE 2

CROSS REFERENCE TO RELATED APPLICATIONS

This application is the National Stage of International Application No. PCT/EP2014/076224 filed on Dec. 2, 2014, which claims the benefit of EP 13195515.5, filed Dec. 3, 2013. The contents of PCT/EP2014/076224 is hereby incorporated by reference in its entirety.

FIELD OF THE INVENTION

The present invention pertains to a vaccine against porcine circo virus type 2 (PCV-2) and to a method of protecting an animal against such an infection using the vaccine.

BACKGROUND ART

PCV-2 is linked to the post-weaning multisystemic wasting syndrome (PMWS) observed in young pigs. This disease was encountered for the first time in Canada in 1991. The clinical signs and pathology were published in 1996, and include progressive wasting, dyspnea, tachypnea, and occasionally icterus and jaundice.

Nayar et al., Can. Vet. J. Volume 38, June 1997 detected porcine circo virus in pigs with clinical symptoms of PMWS and concluded that a PCV, other than the known PCV recognized as a natural inhabitant of PK-15 cells, could be linked to PMWS. Later publications (Hamel et al., J. Virol., 72(6), 5262-5267, 1998; Meehan et al., J. gen. Virol., 79, 2171-2179, 1998) confirmed these findings, and it was proposed (Meehan et al., supra) to refer to the new pathogenic PCV as PCV-2, whereas the original PK-15 cell culture isolate (Tischer et al., Nature 295, 64-66, 1982), should be referred to as PCV-1. PCV-2 is a small (17-22 nm) icosahedral non-enveloped virus containing a circular single stranded DNA genome. The length of the PCV-2 genome is about 1768 bp. PCV-2 isolates originating from different regions in the world seem to be closely related to each other and display 95 to 99% nucleotide sequence identities (Fenaux et al., J. Clin. Micorbiol., 38(7), 2494-2503, 2000). ORF-2 of PCV encodes the capsid protein of the virus. The ORF 2 of PCV 2 encodes a protein of 233 amino acids. The ORF 2 of all PCV-2 isolates share 91-100% nucleotide sequence identity and 90-100% deduced amino acid sequence identity.

A conventional vaccine to prophylactically treat animals, in particular pigs, against an infection with pathogenic porcine circo virus type 2, may be based on whole PCV-2 virus as (non-replicating) immunogen. However, in the case of PCV-2 matters are complicated by the fact that PCV-2 does not replicate to high titers in cell culture. A vaccine based on whole virus as the immunogen is therefore less ideal from a practical (economic) point of view. In the art it has been shown that the ORF2 encoded capsid protein (even when recombinantly expressed) is suitable as a subunit immunogen of porcine circo virus type 2 for use in an adequate vaccine. This can be understood since this subunit, in a circulatory system, shows up the same way as the virus itself, essentially differing in the fact that the DNA and non-structural proteins are not present inside the capsid.

In the art several vaccines against PCV2 are known and commercially available.

Porcilis® PCV (available from MSD Animal Health, Boxmeer, The Netherlands) is a vaccine for protection of pigs against porcine circo virus type 2, for use in pigs from three weeks and older. When given as a two-shot (two dose) vaccine, the duration of immunity (DOI) is 22 weeks, almost completely covering the fattening period of pigs. The vaccination may lead to hyperthermia and other systemic reactions.

Ingelvac CicroFlex® (available from Boehringer Ingelheim, Ingelheim) is a vaccine for protection of pigs against porcine circo virus type 2, for use in pigs from two weeks and older. When given as a one-shot (one dose) vaccine, the DOI is 17 weeks. The vaccination may lead to hyperthermia and on a rare occasion in anaphylactic reactions. Circovac® (available from Merial, Lyon, France) is a vaccine for protection of pigs against porcine circo virus type 2, for use in pigs three weeks and older. When given as a two-shot vaccine, the DOI is only 14 weeks. The vaccination may lead to hyperthermia and other systemic reactions such as reduced feed intake.

Suvaxyn® PCV (available from Zoeitis, Capelle a/d IJssel, The Netherlands) is a vaccine for protection of pigs against porcine circo virus type 2, for use in pigs from three weeks and older. When given as a one-shot vaccine, the DOI is 19 weeks. The vaccination may lead to hyperthermia and other systemic reactions such as vomiting.

Other vaccines are described for example in WO2007/028823, WO 2007/094893 and WO2008/076915. None of them shows a DOI longer than as known from the commercial available vaccines.

OBJECT OF THE INVENTION

The aim of the present invention is to devise a vaccine that can provide a DOI against an infection with pathogenic porcine circo virus type 2 at least as long as existing vaccines, even when an animal at the time of vaccination has circulating antibodies directed against porcine circo virus type 2, the vaccine at the same time being convenient in use and safe for the animals, in particular inducing little or no systemic side effects such as hyperthermia.

SUMMARY OF THE INVENTION

In order to meet the object of the invention a new vaccine has been devised, the vaccine comprising non-replicating immunogen of porcine circo virus type 2, in particular recombinantly expressed ORF2 protein of porcine circo virus type 2, for use in prophylactically treating an animal that has circulating antibodies directed against porcine circo virus type 2, in particular maternally derived antibodies, against an infection with pathogenic porcine circo virus type 2 by a single dose administration of the vaccine into the dermis of the animal.

Surprisingly, it was found that when vaccinating the animal into its dermis with only one dose of a vaccine containing the non-replicating immunogen of porcine circo virus type 2, a very long DOI of 23 weeks against an infection with pathogenic porcine circo virus type 2 can be obtained, even when the animal has medium to high circulating antibodies against porcine circo virus type 2, without any, or hardly any, systemic side effects. This way, a DOI that is even substantially longer than the DOI of any existing one dose vaccine can be obtained. It was in particular surprising since it was found that these antibodies may be maternally derived antibodies.

The invention also enables a method of prophylactically treating an animal that has circulating antibodies directed against porcine circo virus type 2, against an infection with pathogenic porcine circo virus type 2 by a single dose administration of a vaccine comprising non-replicating immunogen of porcine circo virus type 2, in particular recombinantly expressed ORF2 protein of porcine circo virus type 2, into the dermis of the animal. Other methods enable by the invention are: a method wherein the vaccine in addition comprises non-live immunogen of *Mycoplasma hyopneumoniae* to treat the animal against an infection with pathogenic *Mycoplasma hyopneumoniae* bacteria; and a further method wherein the vaccine in addition comprises non-live immunogen of *Lawsonia intracellularis* to treat the animal against an infection with pathogenic *Lawsonia intracellularis* bacteria; a method of prophylactically treating an animal that has circulating antibodies directed against porcine circo virus type 2 against an infection with porcine circo virus type 2 and *Mycoplasma hyopneumoniae*, wherein the method comprises administering to the animal a single dose of a vaccine comprising a non-replicating immunogen of porcine circo virus type 2 into the dermis, in particular recombinantly expressed ORF2 protein of porcine circo virus type 2, and concurrently administering to the animal a single dose of a vaccine comprising non-live immunogen of *Mycoplasma hyopneumoniae* into the dermis; and a method of prophylactically treating an animal that has circulating antibodies directed against porcine circo virus type 2 against an infection with porcine circo virus type 2 and *Lawsonia intracellularis*, wherein the method comprises administering to the animal a single dose of a vaccine comprising a non-replicating immunogen of porcine circo virus type 2, in particular recombinantly expressed ORF2 protein of porcine circo virus type 2, into the dermis, and concurrently administering to the animal a single dose of a vaccine comprising non-live immunogen of *Lawsonia intracellularis* into the dermis.

It is noted that Opriessnig et al. in *Veterinary Microbiology* 131 (2008) 103-114, reports about a research program aiming at establishing whether there is a difference between intradermal and intramuscular PCV2 vaccination. The conclusion drawn by Opriessnig is that "differences between intradermal and intramuscular routes of vaccine administration were not found". In the light of this document, it looks even more surprising that applicants found a significant difference between intradermal and intramuscular vaccination, in particular a significantly different antibody response. With the knowledge of the present invention at hand, a possible explanation for the fact that Opriessnig did not find any differences may be that, without knowing, both vaccines were simply applied intramuscularly. This can be understood as follows: Opriessnig used a Pulse 250™ needleless injection system (Pulse NeedleFree Systems Inc. Lenexa, Kans., USA) to apply the vaccine. This device, although being needle-less, is not especially configured for intradermal application. The producer of this system indicates on the brochure for this device (see pulse-nfs.com), that the device has been designed to administer "through the skin and into the muscle tissue". The injection volume used by Opriessnig, viz. 2 ml, is quite high and typical for intramuscular vaccination. The World health Organization in its Aug. 27, 2009 paper called "Intradermal Delivery of Vaccines; A review of the literature and the potential for development for use in low- and middle-income countries" also indicates that "needle-less" vaccination does not necessarily mean "intradermal" vaccination (see Table 1, Page 3 of the review). Only when a needle-less device is "configured for intradermal vaccination", then a vaccine may indeed be delivered into the dermis. Otherwise it may be delivered subcutaneous or intramuscularly. So given the fact that Opriessnig used a device that is not particularly configured for intradermal vaccination, that she used a large injection volume and more importantly, that she did not find a difference between intradermal vaccination and intramuscular vaccination whereas the present inventors found a substantial difference (in particular with regard to IgM titers), it can only be concluded that Opriessnig simply applied the vaccine reported in her paper as "delivered intradermally" into the muscle of the animals.

It is also noted that it is reported recently that the impact of maternally derived antibodies (MDA) on vaccination effectiveness has not been well studied although the overall impact is believed to be minor (see APVS Vietnam, 23-25 Sep. 2013; Brad Tacker et al: Diagnostic Laboratory Survey of Porcine Circovirus Type 2 and *Mycoplasma* Hyopneumoniae Maternally derived Antibodies). Still, at the same time it is reported that when vaccinating in the presence of medium to high antibody levels two vaccinations are used to make sure that maternally derived antibodies have no impact on PCV2 vaccination efficacy.

WO 2008/076915 (Fachinger et al) describes a one dose PCV2 vaccine approach using CircoFLEX® to acquire active immunity against porcine circo virus type 2, wherein the vaccine is given intramuscularly. The acquired immunity was tested 9 weeks after vaccination. WO 2009/126356 (Roof et al.) describes a one dose PCV2 vaccine approach using CircoFLEX® wherein the vaccine is given intramuscularly. The vaccine is given in MDA negative animals and challenge takes place 4% weeks after vaccination.

WO 2005/009462 (Parisot et al) describes several vaccination approaches against PCV2 based on inactivated PCV2 virus. At first, a one shot IM vaccination approach in MDA negative animals (Example 5). A two shot PCV2 vaccine approach wherein the vaccine is given intramuscularly in MDA negative animals and challenge takes place 5 weeks after vaccination (Example 6). A One shot IM vaccination approach in sows with circulating antibodies, leading to the piglets being protected against PCV2 (Example 7). There is no disclosure of a vaccine comprising recombinantly expressed ORF2 protein, for a single shot administration approach in animals having circulating antibodies against PCV2, in particular maternally derived antibodies, via intradermal administration. Let alone, there is no expectation at all that this may lead to a very long DOI. Although several needleless administration devices are mentioned on page 19, it is not indicated that they can be used for intradermal administration. As is commonly known for example, the mentioned Biojector is devised in particular for IM and SC administration.

WO 00/01409 mentions in Example 17 the preparation of a vaccine comprising inactivated PCV2 virus that can be administered via the intradermal route. This document however fails to show a vaccine comprising recombinantly expressed ORF2 protein, for a single shot administration approach in animals having circulating antibodies against PCV2, in particular maternally derived antibodies, via intradermal administration.

Gamage in Vaccine 27 (2009) 6595-6604 mentions that sera of pigs vaccinated three times with a phage displaying PVC capsid protein are able to neutralize PCV2 virus. There is no showing in Gamage that after the first vaccination there is a protective response, nor is it clear from Gamage whether the injector gun used is indeed capable of intradermal administration. As shown above with regard to Opriessnig, in the art it is often stated that needle-less guns inject into the dermis, but only few injectors are capable of delivering a vaccine actually into the dermis.

EP 1 958 644 mentions features of the present invention as isolated features throughout its specification but fails to show all features of the present invention in combination.

DEFINITIONS

Non-replicating immunogen of a virus is any substance or compound corresponding to the virus, other than the replicating ("live") virus as a whole, against which an immunological response is to be elicited, such that the corresponding virulent virus or one or more of its virulence factors will be recognized by the host's immune system as a result of this immune response and is ultimately neutralized. Typical examples of non-replicating immunogens are killed whole viruses and subunits of these viruses such as capsids and surface expressed proteins, for example recombinantly expressed. A vaccine comprising non-replicating immunogen of a virus differs not only from a "live" virus vaccine, but also from a DNA vaccine in which the DNA is not an immunogen as such, but after incorporation into host cells, expresses the corresponding immunogen.

Prophylactic treatment against an infection with a virus is aiding in preventing or ameliorating an infection resulting from a post treatment challenge with a pathogenic virus, in particular to reduce viral load in the host after such challenge.

Prophylactic treatment against disease resulting from an infection with a virus is aiding in preventing or ameliorating one or more clinical manifestations resulting from a post treatment infection with the virus.

Administration of a vaccine into the dermis means a sufficient amount of the vaccine is deposited in dermis, leading to an immunological response significantly different (in particular: when using the Wilcoxon rank sum test in a test set up as outlined in Example 3, the p value should be less than 0.10, preferably less than 0.05) from an intramuscular administration with the same vaccine and volume thereof. Several devices are commercially available for intradermal vaccination, for example the IDAL® vaccinator (MSD Animal Health), the Pulse 50 MicroDose (Pulse Needle Free Systems), or other devices as described in Vaccine, 2012 Jan. 11; 30(3):523-38 (see in particular Table 1, page 525: "An overview of different devices for liquid and solid formulation administration")

Single dose administration of a vaccine for use in prophylactically treatment means that in order to obtain protective immunity, the vaccination does not need to be boosted with a second administration. In a two-shot regime, the first (prime) vaccination is typically boosted within 6 weeks from the first administration, commonly within 3 or even 2 weeks from the first administration, and only after the second (boost) administration protective immunity may be obtained.

Embodiments of the Invention

In a first embodiment the single dose administration comprises less than 0.5 ml of the vaccine, preferably 0.2 ml of the vaccine. A dosage below 0.5 ml appears to be suitable for intradermal vaccination. At such a low dosage the dermis remains at least to a sufficient extent intact and available for receiving the vaccine, whereas at a substantially higher dosage, there is a risk of rupturing the dermis, leaving the dermis unavailable for receiving the vaccine.

In a next embodiment the vaccine is administered with a needle-less vaccination device, using a jet of the vaccine to reach the dermis through the skin of the animal. Vaccination into the dermis is in this embodiment provided by a needle-less vaccination device using a liquid jet of the vaccine (a high pressurized fluid stream), typically using a very low volume of vaccine in the range of 0.05 to 0.2 ml. This further increases the safety of the vaccine and method of administration.

In another embodiment the non-replicating immunogen is recombinantly expressed ORF2 protein of porcine circo virus type 2, for example expressed by baculo virus as known in the art, or in a PCV1-PCV2 chimeric virus. This recombinant protein has proven to be suitable for application in the present invention. In particular, the ORF2 protein can be expressed in a baculo virus expression system such as described in WO2007/028823, WO 2007/094893 or WO2008/076915.

In still another embodiment the animal at the time of administration has circulating antibodies at a titer of 7 log 2 (7 units of a 2 log) or above (established according to the method as described here beneath under Example 1, "Serology"). It was found that even at this medium to high antibody titer, the present invention is still effective.

In an embodiment the single dose of the vaccine comprises less than 5000 AU of the immunogen (the minimum amount being an amount still leading to an effective immune response). It was found that at this dose, lower than the dose in the existing vaccine PORCILIS® PCV (a vaccine comprising porcine circovirus type 2 ORF2 subunit antigen, licensed with a two shot vaccination regime to reach a DOI of 22 weeks), one can still obtain a DOI of more than 23 weeks after only one vaccination. In an embodiment the single dose of the vaccine comprises about 2000 AU of the immunogen. This amount appears to be sufficient to obtain the advantages of the present invention.

In another embodiment the vaccine comprises non-live immunogen of *Mycoplasma hyopneumoniae* to treat the animal against an infection with pathogenic *Mycoplasma hyopneumoniae* bacteria, and/or the vaccine comprises non-live immunogen of *Lawsonia intracellularis* to treat the animal against an infection with pathogenic *Lawsonia intracellularis* bacteria.

In still another embodiment the vaccine comprises an adjuvant comprising mineral oil, characterised in that the amount of mineral oil in the vaccine is between 1 and 10% v/v (volume of oil over total volume of the vaccine). It is commonly known that mineral oil is a very good potentiator of the immune response (also referred to as "adjuvant"). However, in pigs it often leads to severe local reactions (swellings having a mean diameter of more than 5 cm), in particular if administered intradermally. It was surprisingly found that with the current intradermal route of vaccination, such severe local reactions may not occur at all, and the mean diameter of the swellings may even stay below 3 cm which is found to be acceptable. In a further embodiment the amount of mineral oil is between 2.5 and 5% v/v. It was found that even at this very low concentration of mineral oil, the immune response was effective.

In embodiments of the method according to the invention an animal receives a single dose administration of a vaccine comprising non-replicating immunogen of porcine circo virus type 2 into the dermis, and concurrently (that is within one day, preferably within a few hours, minutes or seconds) receives a single dose administration of a vaccine comprising non-live immunogen of *Mycoplasma hyopneumoniae* (Mhyo) into the dermis to treat a porcine circo virus type 2 infection and an *Mycoplasma hyopneumoniae* infection at the same time. Several non-live *Mycoplasma hyopneumoniae* immunogens to be used in this or any of the other embodiments of the invention are known in the art such as bacterins (Swine Health and Production. 1998; 6(3):107-112), recombinantly expressed Mhyo antigens (Infection and Immunity, June 1997 vol. 65 no. 6 2502-2507), the soluble fraction of an Mhyo culture (WO 2013/152083) etc.

In another embodiment an animal receives a single dose administration of a vaccine comprising non-replicating immunogen of porcine circo virus type 2 into the dermis, and concurrently receives a single dose administration of a vaccine comprising non-live immunogen of *Lawsonia intracellularis* into the dermis to treat a porcine circo virus type 2 infection and an *Lawsonia intracellularis* infection at the same time. With regard to *Lawsonia intracellularis* immunogens to be used in this or any of the other embodiments of the invention, several types of non-live immunogen are known in the art, and are for example described in WO2009/144088 (killed whole cell immunogen), WO2005/070958 (sub-units) and WO97/20050 (killed whole cell immunogen). Combination with PCV and Mhyo antigens as such is described in WO2009/144088.

Examples

Example 1 is an experiment to show that a single dose intradermal vaccination can provide twenty three weeks of immunity against an infection with porcine circo virus type 2.

Example 2 is another experiment with a PCV2 ID once vaccination approach showing that vaccination is safe and leads to protective titers.

Example 3 is a direct comparison between intradermal and intramuscular vaccination.

Example 4 describes experiments with combined intradermal vaccination.

Example 5 describes an experiment with combination vaccines, various antigen dosages and various adjuvants.

Figure 1:
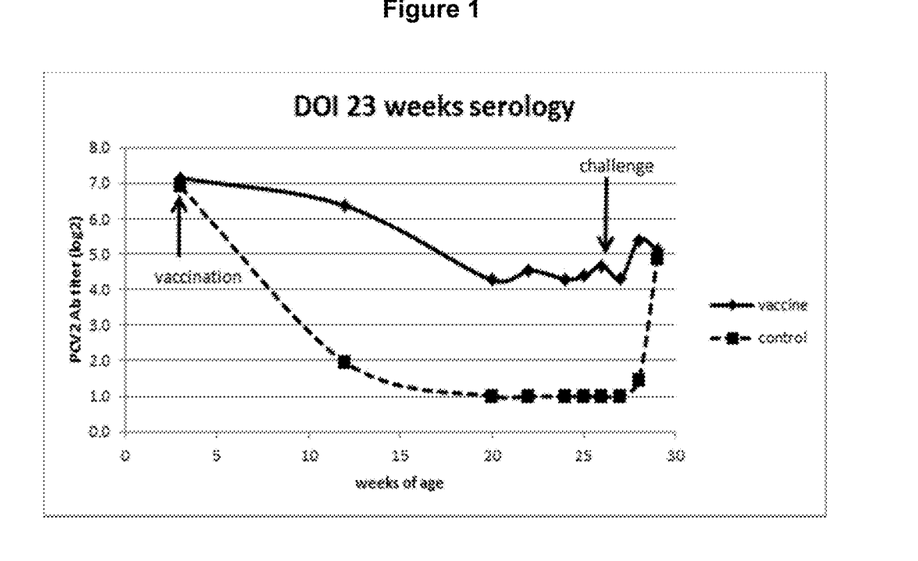
FIG. 1 depicts the serology in a DOI study.
Figure 2:
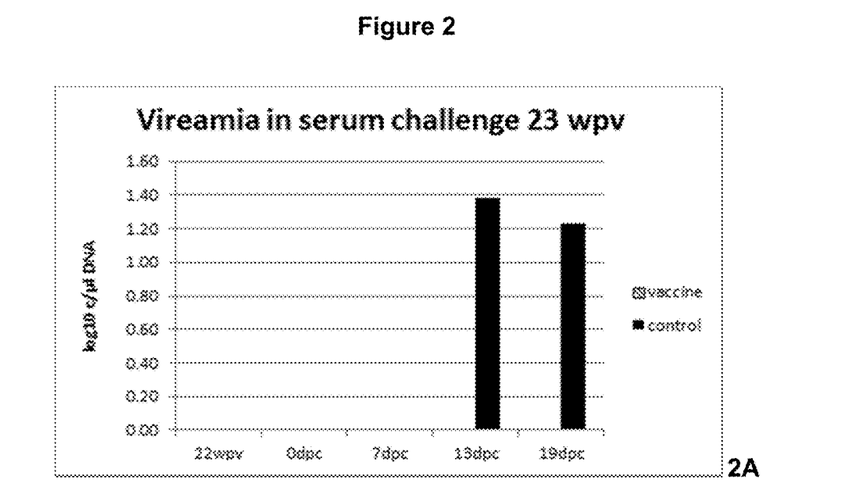
FIGS. 2A-2C show the viral load in serum, feces, and in organs, respectively.
Figure 3:
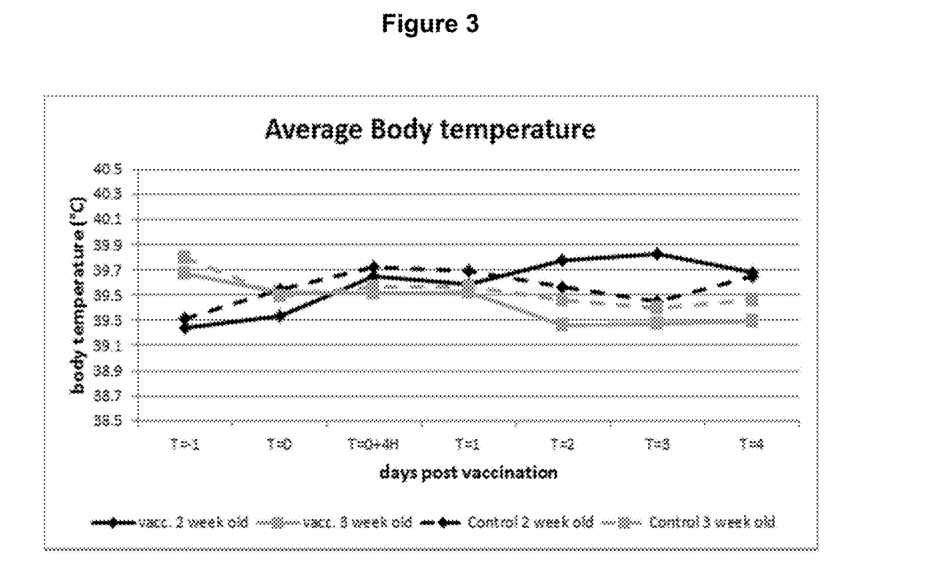
FIG. 3 shows the average body temperatures in days, post vaccination.
Figure 4:
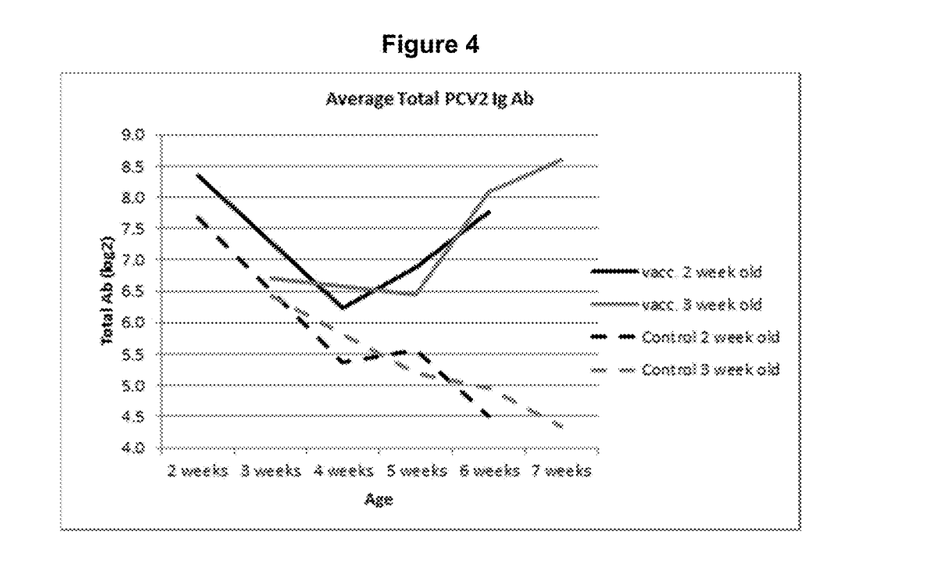
FIG. 4 depicts the average total PCV2 Ig Ab results.
Figure 5:
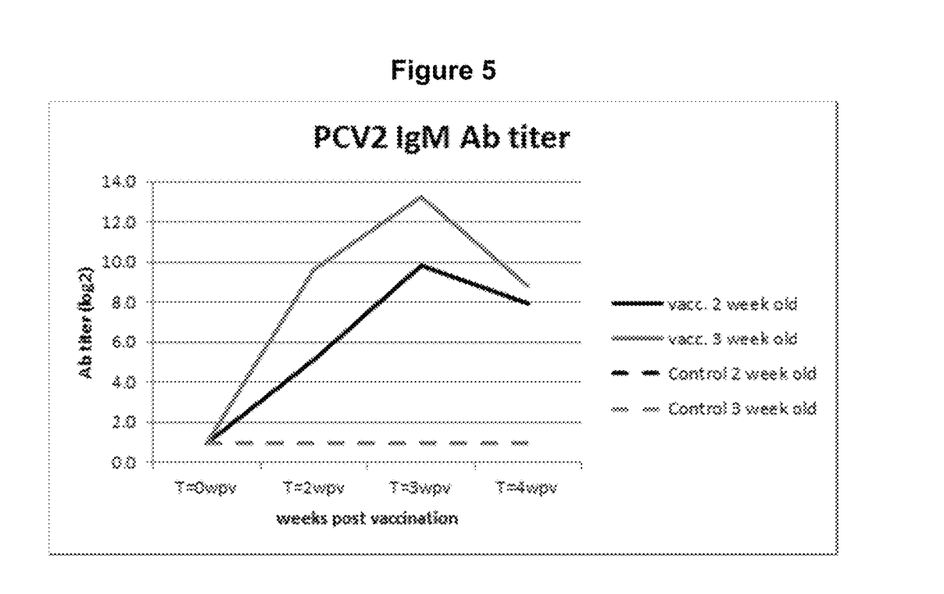
FIG. 5 shows the average PCV2 IgM Ab results.
Figure 6:
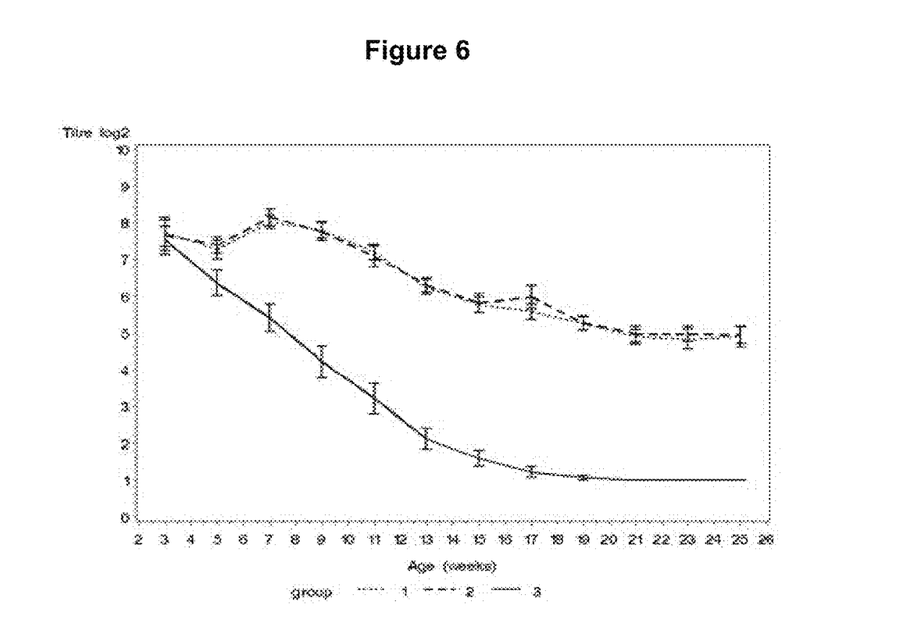
FIG. 6 depicts the antibody titers in a duration study.
Figure 7:
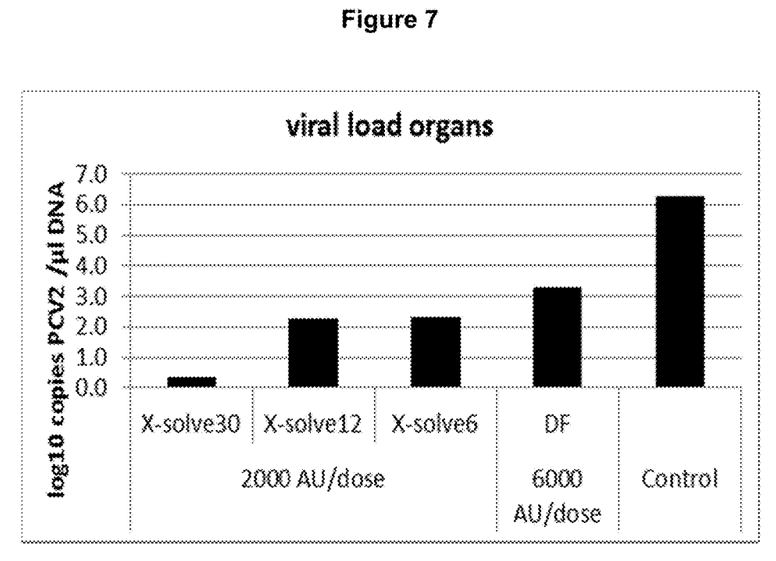
FIG. 7 shows the viral load in the organs.
Figure 8:
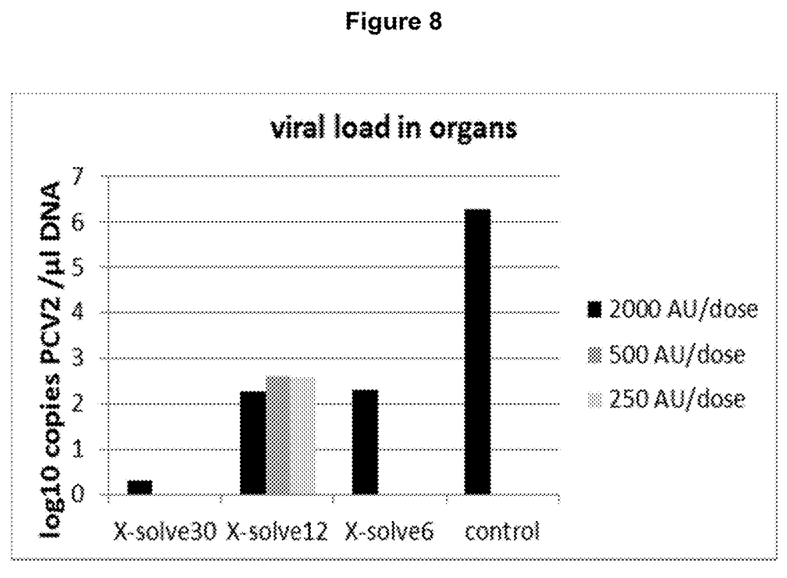
FIG. 8 depicts the viral load in the organs.

FIG. 1 Serology in a DOI study
FIG. 2 Viral load in serum, feces and organs
FIG. 3 Average body temperatures
FIG. 4 Average total PCV2 Ig Ab results
FIG. 5 Average PCV2 IgM Ab results
FIG. 6 Antibody titers in a duration study
FIG. 7 Viral load in organs
FIG. 8 Viral load in organs Example 1

Experimental Design

Progeny of 10 sows with antibodies against PCV2 were used for this study. Piglets were divided across litters into 2 groups of 15 animal animals. At 3 weeks of age, the piglets of group 1 were vaccinated intradermally on the right side of the neck with 0.2 ml of a vaccine comprising recombinantly expressed ORF2 protein of porcine circo virus type 2 (see WO 2007/028823 for the provision of the protein), using the commercially available intradermal vaccination device IDAL® (available from MSD Animal Health, Boxmeer, The Netherlands), while group 2 was left unvaccinated and served as a control group. All study animals were observed daily for clinical signs. Blood samples of all animals were taken at time of vaccination, 9, 17, 19 and 21 weeks later. Twenty-three weeks following vaccination each animal was challenge infected using a wild-type PCV2 challenge virus strain applied intranasally.

Serum samples and fecal swabs were taken one day before challenge and one, two and three weeks after challenge and were examined for PCV2 viral nucleic acid by quantitative PCR. In addition serum samples were examined for PCV2 antibodies. Three weeks following challenge, all animals were necropsied and inguinal lymph node, tonsil and lung were sampled for determination of PCV2 viral antigen and nucleic acid.

The vaccine used was given as an oil-in-water emulsion, comprising 5% v/v of the mineral oil MARCOL® 52 (Exxon), 0.30% w/v vitamin E acetate and 0.32% Polysorbate 80 (TWEEN® 80; Sigma Aldrich), water for injection and 2000 AU of PCV2 protein per 0.2 ml. The AU units are calculated based on an AlphaLISA test of PerkinElmer. For this test the wells of a polystyrene microtitre-plate are filled with serial dilutions of test sample containing PCV2 ORF2 antigen alongside serial dilutions of a reference standard. These dilutions are incubated with acceptor-beads (coated with monoclonal antibody directed against PCV2 ORF2), and biotin-labeled secondary antibody which is also directed against PCV2 ORF2. The amount of bound secondary antibody is then quantified by incubation with streptavidin coated donor-beads and chemiluminescent detection. The reference standard is such that the commercially available vaccine Porcilis® PCV is set to contain 5000 AU per (2 ml) dose.

Experimental Procedure

Daily Observation

All pigs were observed daily for clinical signs of disease. Observations consisted of systemic reactions including loss of appetite, tendency to lie down, listlessness or drowsiness, shivering, bristling, oedema (especially around the eyes), vomiting, diarrhoea and dyspnoea.

Sampling of Blood

Blood samples were collected before vaccination, 9, 17, 19 and 21 weeks later. Blood samples were collected one day before challenge and 7, 13 and 19 days after challenge. This was done from all pigs individually.

Fecal Swabbing

Fecal swabs were taken from all animals, using one dry swab per animal, one day before challenge, 7, 13 and 18 days post challenge. Swabs were taken using standard procedures, into medium containing antibiotics. Suspensions of swabbed material in medium was clarified by centrifugation, aliquotted and stored at $\leq -18°$ C. until further use.

Serology

All serum samples were examined for antibodies against PCV2, using standard ELISA procedures. In brief, serially diluted serum samples were incubated on microtiter plates coated with baculovirus expressed PCV2 ORF2 antigen. After removing the sera, all wells were incubated with a fixed amount of biotin-labeled PCV2-specific monoclonal antibody. Bound MoAb was then incubated with peroxidase-conjugated streptavidin followed by chromophoric detection. Titers were expressed as log 2 titers.

Postmortem Examination

At the end of the experiment all animals were euthanized by bleeding following stunning. During necropsy the animal was opened and the viscera are inspected in-situ, paying particular attention to the following organs: lungs, inguinal and mesenteric lymph nodes, tonsils, thymus, spleen, liver and kidneys. Following this, samples from tonsil, lung (lobus accessories), and inguinal lymph node were removed for quick freezing and later analysis by quantitative PCR (qPCR).

Quantitative PCR

Quantitative PCR (qPCR) was performed on all sera and fecal swabs, and on 10% tissue homogenates of tonsil, lung and inguinal lymph nodes. In brief, DNA was extracted from the samples using a commercial kit. PCV2 genomic DNA in each sample was quantified by polymerase chain reaction (PCR), using primers and a dually labeled hydrolysis probe specific for PCV2. The cycle number where specific fluorescence exceeded the threshold was correlated with the cycle numbers for a set of samples containing known amounts of a PCV2-containing plasmid. Results were expressed as log 10 copies/µl of reaction mixture (log 10 c/µl).

Results

At the start of the experiment all animals were found to be healthy. In the control group one animal was found dead at 6 weeks post vaccination (wpv). Two vaccinated animals had slight local problems, viz. a slight motional dysfunction (stiffness in one leg). Given the low problem, these animals were not treated. None of the vaccinated animals showed any signs of disease or systemic reactions such as hyperthermia, reduced feed intake, anaphylactic shock or vomiting.

The results of the serology are given in FIG. 1. It is clear that the vaccinated animals keep an anti-PCV2 titer that seems to level out to about 4.0 log 2, whereas in the control animals the titer decreases below the detection limit. After challenge (23 wpv, at an age of 26 weeks), titers slightly rise in the vaccinated group. In the control group titers rise to the same level.

The qPCR results are shown in FIGS. 2A, 2B and 2C ("dpc"=days post challenge). It appears that the vaccinated animals, 23 weeks after vaccination were protected from challenge infection with PCV2, as shown by the significant reduction of PCV2 nucleic acid in serum, lymphoid organs and lung. Furthermore, the vaccine was capable to reduce the viral shedding as demonstrated by a significant reduction of the viral load in fecal swabs against PCV2 of at least 23 weeks. This was done in field animals, having circulating anti-body titers against PCV2 of approximately 7 log 2, which is considered a medium level.

Example 2

Experimental Design

A total of 46 piglets from one farrowing batch were allotted to 4 treatment groups: two vaccinated groups of 13 piglets each and two control groups of 10 piglets. Group one was vaccinated as indicated above under Example 1 when the piglets were approximately two weeks old, group two was vaccinated when the piglets were approximately three weeks old. The piglets were intradermally vaccinated in the right side of the neck with a single dose of vaccine. Groups 3 (control group 2 week old animals) and 4 (control group 3 week old animals) were not vaccinated. Serum samples were collected from all animals on the day of vaccination, 2, 3 and 4 weeks after vaccination. Temperatures were taken one day before vaccination, at the day of vaccination and four hours later and at 1, 2, 3, 4 days post vaccination.

Experimental Procedure

Before vaccination, the piglets were observed for general health. Body temperatures were taken of all piglets, on day T=-1, day T=0 at 0 and 4 hours after vaccination, and on day T=1, 2, 3, 4 post vaccination.

Blood samples were collected on the day of vaccination and 2, 3 and 4 weeks later. This was done from all pigs individually according to standard procedures. The blood samples were collected without the addition of anti-coagulant. Serum was prepared from the clotted blood samples and aliquots were filled and stored at -20° C. until analysis.

Total PCV2 Ig antibody and PCV2 IgM antibody ELISA were tested as indicated here above under Example 1 ("Serology"), except that in the case of IgM antibody ELISA, the plates were coated with IgM antibody and thereafter incubated with PCV2 ORF2 antigen, before incubation with a fixed amount of biotin-labeled PCV2-specific monoclonal antibody.

Results

At the start of the experiment all animals were found to be healthy. Average results of the body temperatures are shown in FIG. 3. No difference could be seen in the average increase in body temperature between either the two and three week old animals (maximum average increase was between 0.0-0.3° C.). Also, the maximum increase in body temperature of individual animals in group 1 and in group 2 was comparable to the maximum temperature increase of individual animals in the two control groups.

Total PCV2 Ig Antibody ELISA

Average results of the total PCV2 Ig antibody response are summarized in FIG. 4. At the time of vaccination, piglets vaccinated at 2 weeks of age had higher (most likely maternally derived) PCV2 antibody titers than piglets vaccinated at 3 weeks of age. The vaccinated animals showed an increase in titer considerably higher than the control animals.

PCV2 IgM Antibody ELISA

Average results of the PCV2 IgM antibody response are shown in FIG. 5. At the time of vaccination all animals were negative for IgM antibodies. Following vaccination the three week old animals had a considerable faster and higher IgM antibody response than the two week old animals. The control animals remained negative throughout the study.

Based on these results it may be concluded that the one dose intradermal vaccination of piglets at 2 and 3 weeks of age resulted in an acceptable safety profile and a good serological response. Comparable results were obtained with another experiment (data not shown) where the starting level of circulating anti-body titers was even higher, viz. up to 9.4 log 2, which is considered to be at the high end of a medium range.

Example 3

Experimental Design

A total of 40 piglets were allotted to four treatment groups of 10 piglets each. Piglets from groups 1 and 2 were intradermally vaccinated with a single dose of vaccine as indicated hereabove under Example 1. The difference between group 1 and 2 was that the IDAL vaccinator of group 2 had a slightly higher pressure build-up (125% of the value of the IDAL vaccinator used for group 1). Piglets from group 3 were intramuscular vaccinated with a single dose of the same vaccine, in the same amount at the same place (in the neck), and piglets from group 4 were left untreated.

Serum samples were collected from all animals on the day of vaccination, three and five weeks after vaccination.

Experimental Procedure

Before vaccination, the piglets were observed for general health, according to standard procedures. Sampling of blood and serology of total anti-PCV2 antibodies and PCV2 ORF2 specific IgM antibodies was done according to the procedure as indicated here above under Example 2.

Results

At the start of the study all animals were found to be healthy. Results of the serology are summarised in Table 1 (titers expressed as log 2). At the time of vaccination mean antibody titers were relatively high. Following vaccination, none of the animals showed an increase in PCV2 Ab titer. At 3 and 5 weeks post vaccination, in the ID groups higher mean PCV2 antibody titers than in the IM group could be observed.

TABLE 1

Average antibody results

| Groups | Titer 0 wpv | Titer 3 wpv | Titer 5 wpv |
|---|---|---|---|
| 1 | 8.2 | 7.3 | 6.2 |
| 2 | 8.3 | 7.0 | 5.9 |
| 3 | 8.6 | 6.5 | 5.1 |
| 4 | 8.4 | 6.2 | 4.3 |

Results of the anti PCV2 IgM serology are summarised in Table 2 (titers expressed as log 2). At three weeks post vaccination anti PCV2 IgM antibody titers of the two ID groups were considerably higher than of the IM group and the control group.

TABLE 2

Average anti PCV2 IgM antibody results

| Group | IgM titer 3 wpv |
|---|---|
| 1 | 12.7 |
| 2 | 8.9 |
| 3 | 3.4 |
| 4 | 1.0 |

When applying the Wilcoxon rank sum test, the p values for the difference in IgM response for each of the ID groups (1 and 2) versus the IM group (3) was below 0.05, viz. 0.0001 and 0.0329 respectively.

Example 4

Progeny of several sows with antibodies against PCV2 were available for this study. Piglets were divided across litters into 3 groups of 18 animals. At 3 weeks of age, the piglets of group 1 and 2 were vaccinated intradermally as indicated here above under Example 1. The animals in group 2 were vaccinated intradermally at the same time with the commercially available vaccine Porcilis® M Hyo ID Once (containing an Mhyo bacterin) according to manufacturer's instructions at the other side of the neck. Animals of group 3 (control group) remained untreated. All study animals were observed daily. Serum samples were taken at the time of vaccination and every other week until animals were sent to slaughter (23-25 weeks of age). These samples were examined for PCV2 antibodies.

Experimental procedures were as indicated here above under Example 1. The resulting serology is shown in FIG. 6.

From this figure it becomes clear that the anti-PCV2 titers remain well above the level of 4 log 2 as established with the experiments as described under Example 1 and found to be protective. There is no indication of negative interference between the vaccines.

This experiment was repeated to check protection against virulent *Mycoplasma hyopneumoniae*. For this repeat experiment sixty piglets were used. Forty animals were vaccinated at the age of 18-24 days with the Mhyo vaccine and twenty of these animals were also vaccinated with the PCV vaccine. Twenty animals were not vaccinated and served as challenge controls. Three weeks after vaccination all animals were infected with a virulent *M. hyopneumoniae* strain and three weeks post-challenge all animals were post-mortem investigated for lung lesions. Lung lesion scores (LLS) were compared between the groups.

The LLS for the groups vaccinated with Porcilis® M Hyo ID Once were significantly lower than those of the control group (p<0.05, Dunn's test). There was no significant difference between the groups that had been vaccinated with Porcilis® M Hyo ID Once alone or in association with the PCV vaccine. It may thus be concluded that the combined vaccination has no negative effect on the immunity obtained with Porcilis® M Hyo ID Once.

Example 5

In total eight vaccines were formulated containing PCV2 (250 to 6000 AU/0.2 ml), M hyo (at the same level as in Porcilis® Mhyo ID Once) and *Lawsonia* antigen (see WO 20089/127684, example 2 for the killed whole cells antigens: at a level of approximately $1 \times 10^9$ cells per 0.2 ml). The vaccines contained different adjuvants. Some vaccines used the existing adjuvant Diluvac Forte (MSD Animal Health, Boxmeer, The Netherlands; called "DF"). Others used the adjuvant formulation as described here above under Example 1 (called "X-solve 12"), or adjuvants formulated with the same constituents as X-solve 12, but at half of the concentrations (called "X-solve 6"), or 2% times the concentrations as in X-solve 12 (called "X-solve 30"). The resulting vaccines were as follows (the Mhyo and *Lawsonia* antigens are not recited; content per dose):

Group 1: 2000 AU PCV2/X-solve 30
Group 2: 250 AU PCV2/X-solve 12
Group 3: 500 AU PCV2/X-solve 12
Group 4: 2000 AU PCV2/X-solve 12
Group 5: 2000 AU PCV2/X-solve 6
Group 6: 500 AU PCV2/DF
Group 7: 2000 AU PCV2/DF
Group 8: 6000 AU PCV2/DF The progeny of 8 sows were used for this study. The piglets had moderate (medium level) maternally derived antibodies (MDA) against PCV2 (average: 6.7 log 2). At three/four weeks of age the piglets from groups one through eight were vaccinated intradermally with a single dose, using an IDAL® vaccinator. Piglets from group nine remained unvaccinated. At seven weeks post vaccination all animals were transported to the challenge facilities. One day later all animals were challenge infected with a challenge strain of PCV2. All piglets were observed daily for clinical signs.

Local reactions were monitored by palpation, starting on the day of vaccination and every two days after vaccination until twenty days post vaccination.

Blood samples were collected from all animals on the day of vaccination and three weeks later, one day before challenge, 1 and 2 weeks later and at the time of necropsy. Serum samples taken from each animal were tested for antibodies against PCV2 and M hyo. During necropsy, mesenteric and inguinal lymph node, tonsil and lung were sampled for quantification of PCV2 nucleic acid.

Experimental procedures were the same as described here above under Example 2. PCV2 IgM antibody response at time of vaccination was below detection level for all groups (below 2.0 log 2). At 3 weeks post vaccination the PVC antibody titer was the highest for the 2000 AU PCV2/X-solve 30 vaccine, viz. 20 log 2. The X-solve 12 groups, comprising 250-, 500- and 2000 AU PCV2 antigen per dose had a titer of 9, 16 and 19 log 2 respectively. The group that received the 2000 AU/X-solve 6 vaccine had a titer of 15 log 2. The DF groups comprising the 500-, 2000- and 6000 AU of PCV2 antigen per dose had a titer of 8, 14 and 16 log 2 respectively. The controls had a titer below detection level.

In this study, systemic and local reactions were assessed. No systemic reactions attributable to vaccination were observed. As far as local effects are concerned, no more than three vaccinated animals (having received the X-solve 12 500 and 2000 AU, or DF 6000 AU PCV2 per dose vaccine respectively) had slight motility problems, the same number as in the control animals. Therefor these reactions may reasonably be regarded as unrelated to the vaccination. With regard to other local reactions, many animals (between about 60-100%) vaccinated with X-solve showed local reactions, the average size of the swellings was less than 3 cm, viz. between 1-2 cm, and the swellings disappeared within 2-6 days. Using DF, only about 30% of the animals showed local swellings, the mean size being less than 0.5 cm, and they disappeared within a day.

In FIGS. 7 and 8 the viral load in the organs (averaged) is depicted for the various vaccines. It appears that all vaccines are able to substantially (in these cases at least 3 logs) reduce the viral load in the relevant organs.

In this study it appeared that all adjuvants used were safe, induced an anti PCV2 IgM response and were able to treat an animal against an infection with pathogenic porcine circo virus type 2. No negative interference between the different antigens was found.

The invention claimed is:

1. A method of prophylactically treating an animal against an infection with pathogenic porcine circo virus type 2 comprising administering a single dose of a vaccine comprising recombinantly expressed ORF2 protein of porcine circo virus type 2 and a *Lawsonia intracellularis* antigen into the dermis of an animal that has circulating antibodies directed against porcine circo virus type 2; wherein the vaccine is administered with a needle-less vaccination device.

2. The method of claim 1, wherein the single dose administration comprises less than 0.5 ml of the vaccine.

3. The method of claim 2, wherein the single dose administration comprises less than 0.2 ml of the vaccine.

4. The method of claim 1, wherein the vaccine comprises an adjuvant comprising mineral oil, wherein the amount of mineral oil in the vaccine is between 1 and 10% v/v.

5. The method of claim 3, wherein the vaccine comprises an adjuvant comprising mineral oil, wherein the amount of mineral oil in the vaccine is between 1 and 10% v/v.

6. The method of claim 5, wherein the amount of mineral oil is between 2.5 and 5% v/v.

* * * * *